United States Patent
Guendel (10) Patent No.: US 7,796,131 B2
(45) Date of Patent: Sep. 14, 2010

(54) METHOD OF VIRTUAL ENDOSCOPY FOR MEDICAL 3D IMAGE DISPLAY AND PROCESSING, COMPUTED TOMOGRAPH, WORKSTATION AND COMPUTER PROGRAM PRODUCT

(75) Inventor: Lutz Guendel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1214 days.

(21) Appl. No.: 11/144,831

(22) Filed: Jun. 6, 2005

(65) Prior Publication Data
US 2005/0272999 A1 Dec. 8, 2005

(30) Foreign Application Priority Data
Jun. 7, 2004 (DE) .................. 10 2004 027 709

(51) Int. Cl.
*G06T 17/20* (2006.01)
*G06T 1/00* (2006.01)
(52) U.S. Cl. ........................ 345/423; 345/418
(58) Field of Classification Search .................. None
See application file for complete search history.

(56) References Cited

U.S. PATENT DOCUMENTS

| | | | |
|---|---|---|---|
| 6,212,420 B1 | 4/2001 | Wang et al. | |
| 6,366,800 B1* | 4/2002 | Vining et al. | 600/425 |
| 6,608,628 B1 | 8/2003 | Ross et al. | |
| 6,928,314 B1* | 8/2005 | Johnson et al. | 600/407 |
| 7,167,180 B1* | 1/2007 | Shibolet | 345/474 |
| 7,551,761 B2* | 6/2009 | Geiger et al. | 382/128 |
| 2001/0031920 A1 | 10/2001 | Kaufman et al. | |
| 2003/0152897 A1* | 8/2003 | Geiger | 434/262 |
| 2004/0209234 A1 | 10/2004 | Geiger | |
| 2005/0117787 A1* | 6/2005 | Iordanescu et al. | 382/128 |
| 2005/0152588 A1* | 7/2005 | Yoshida et al. | 382/128 |

OTHER PUBLICATIONS

M. Wan, Z. Liang, Q. Ke, L. Hong, I. Bitter, and A. Kaufman, "Automatic centerline extraction for virtual colonoscopy," IEEE Trans. Med. Imag., vol. 21, pp. 1450-1460, Dec. 2002.*
D. Bartz, "Virtual Endoscopy in Research and Clinical Practice," Eurographics State-of-the-Art-Reports 2003.*
Willi A. Kalender: "Computertomographie—Grundlagen, Gerätetechnologie, Bildqualität, Anwendungen"; Publicis MCD Verlag, 2000; S. 147-157.
David Jocha, Jozsef Koloszar: "Interactive Virtual Colonoscopy", Computer Graphics Research Group, Budapest/Hungary, in: Radiology, vol. 199, May 1996, 12 Seiten; Internet: http://www.cg.tuwlen.ac.at/studentwork/CESCG/CESCG-2001/DJochaJKoloszar/paper.pdf.

(Continued)

*Primary Examiner*—Daniel F Hajnik
(74) *Attorney, Agent, or Firm*—Harness, Dickey & Pierce, P.L.C.

(57) ABSTRACT

A method is proposed for virtual endoscopy for medical 3D image display and processing in computed tomography. The method includes providing a first evaluation volume on the basis of a 3D data volume and providing an observer path through the first evaluation volume. To allow automatic calculation of the observer path, even for the case in which no continuous path can be found through the evaluation volume, the present concept has provision for automatic ascertainment of at least one further evaluation volume, which is separate from the first evaluation volume, on the basis of the 3D data volume according to predetermined criteria.

17 Claims, 3 Drawing Sheets

OTHER PUBLICATIONS

German Office Action issued Sep. 9, 2004.
Dean G. Assimos, David J. Vining. Virtual Endoscopy. Journal of Endourology. 2001, 15(1):47-51. Mary Ann Liebert, Inc., NY.
J. Rodenwaldt, L. Kopka, R. Roedel, A. Margas, E. Grabbe. 3D Virtual Endoscopy of the Upper Airways: Optimization of the Scan Parameters in a Cadaver Phantom and Clinical Assessment. Journal of Computer Assisted Tomography. 1997, 21(3):405-411. Lippincott, Williams & Wilkins, PA.
Canadian Office Action dated Aug. 3, 2007.
Indian Office Action, (Aug. 2007).

* cited by examiner

METHOD OF VIRTUAL ENDOSCOPY FOR MEDICAL 3D IMAGE DISPLAY AND PROCESSING, COMPUTED TOMOGRAPH, WORKSTATION AND COMPUTER PROGRAM PRODUCT

The present application hereby claims priority under 35 U.S.C. §119 on German patent application number DE 10 2004 027 709.5 filed Jun. 7, 2004, the entire contents of which is hereby incorporated herein by reference.

FIELD

The invention generally relates to a method of virtual endoscopy for medical 3D image display and processing. More preferably, it relates to a method including a first evaluation volume being provided on the basis of a 3D data volume, an observer path being provided through the first evaluation volume. The invention also generally relates to a computed tomograph, a workstation and/or a computer program product.

BACKGROUND

Modern medical imaging methods normally provide images in digital form. To this end, the first step within the framework of "primary applications" is data recording and the provision of the digital data in the course of data construction. In particular, computed tomography images are provided in digital form and can thus be processed further directly in a computer or in a workstation. From the original images, it is possible to obtain images in a new orientation with two-dimensional or three-dimensional display (2D display, 3D display) in order to provide a suitable overview for the examiner. Such displays are intended, in particular, to form the basis of subsequent diagnosis within the context of a monitor examination.

Advantages of computed tomography result, in particular, from the fact that there are no superposition problems as in the case of conventional radiography. Further, computed tomography provides the advantage of undistorted display regardless of different magnification factors associated with the recording geometry in radiography.

In the meantime, a series of different procedures have become established for 3D image display and processing. For these procedures, a computed tomograph has suitable control elements, e.g. a computer mouse or other control media. A workstation for image display and processing of computed tomography images is equipped with appropriate software in the form of a computer program product and a user interface on a screen with appropriate control elements to which functions are assigned.

Computed tomography (CT) first of all normally provides two-dimensional sectional images of the transverse plane of a body to be examined as direct recording plane. In this case, the transverse plane of a body is arranged essentially at right angles to the longitudinal axis of a body. Two-dimensional sectional images in a plane at an angle that has changed in comparison with the transverse plane and/or those which are calculated with a different, particularly broader, layer thickness than the original layer thickness are normally called multiplanar reformations (MPR).

One option which is fundamental to diagnosis is interactive inspection and evaluation of the image volume, usually under the control of an appropriate control element. The examiner can use such control elements—in a similar manner to guiding a sound head in ultrasound—to feel his way to anatomized structures and pathological details and can move forward and backward to select that image in which a detail of interest is presented most clearly, that is to say by way of example is displayed with the highest contrast and the largest diameter.

An extended form of two-dimensional display involves putting together layers (slabs) of arbitrary thickness from thin layers. For this, the term "sliding thin slab" (STS) has become established.

All 2D displays have the advantage that the computed tomography values are displayed directly and without corruption. Any interpolations or averages formed over a plurality of layers are negligible in this case. Thus, there is always simple orientation in the evaluation volume, which is also called the volume of interest (VOI), and in the associated 3D data volume and also explicit interpretability of the image values. This type of monitor examination is work-intensive and time-consuming, however.

By contrast, the most realistic presentation of the evaluation volume possible can be achieved through three-dimensional display of the evaluation volume. Although 3D image display and processing is normally the prerequisite for specific elaboration of diagnostically relevant details, the latter examination is normally performed in a 2D display.

In the case of 3D image display and processing, a 3D data volume is normally provided which is taken as a basis for displaying the evaluation volume. The examiner preferably prescribes an observer position from which he wishes to observe the evaluation volume. In particular, the examiner normally has a search beam at his disposal. In this example, a two-dimensional image is calculated which is at right angles to the search beam and is intended to convey a spatial impression.

To construct such a display pixel by pixel (also: voxel—acronym for volume element) in the image plane, all CT values along the search beam through the 3D data volume need to be taken into account and assessed for each beam from the observer to the respective pixel. The examiner normally prescribes a pixel value, e.g. a contrast value, which he selects in suitable fashion for displaying a pixel. The repetition (inherent to the method) of this process shows the examiner a collection of pixels corresponding to the search beam on the basis of the prescribed pixel values within the context of a CT value profile for the search beam, that is to say shows a 3D display of the body region/evaluation volume of interest (VOI).

All 3D displays may, that is to say within the context of a secondary application, be designed either as a central projection or as a parallel projection. For a parallel projection, "maximum intensity projection" (MIP) or generally "volume rendering" (VR) is particularly suitable.

In the case of MIP, the pixel with the highest CT value is determined in the projection direction along the search beam. In that case, the pixel value thus corresponds to the maximum CT value on the search beam.

In the case of VR, not just a single pixel is chosen for each individual search beam coming from the observer's eye. Rather, all CT values along the search beam can, with suitable weighting, deliver a pixel as a contribution to the resulting image.

Freely selectable and interactively alterable transfer functions are used to assign opacity and color to each pixel value. It is thus possible, by way of example, to select normal soft tissue to be largely transparent, contrasted vessels to be slightly opaque and bones to be very opaque. Preferable central projections may be attained, by way of example, by "surface shaded display" (SSD) or by "perspective volume rendering" (pVR) (or else "virtual endoscopy"). Accordingly, there is the SSD or else the pSSD used in virtual endoscopy.

SSD is threshold-based surface display, where a pixel is prescribed by prescribing a pixel value in the form of a threshold. For every search beam through the present 3D data volume, that pixel is determined at which the prescribed pixel value in the form of a threshold value is reached or exceeded for the first time as seen by the observer.

One basic difference between SSD and VR is that in the case of SSD only one threshold is defined, but the surface is displayed opaque. In the case of VR, on the other hand, a plurality of threshold regions are defined and these are assigned colors and transparencies.

"Virtual endoscopy" is intended to permit a perspective view of the close surroundings of the virtual "endoscope head". Unlike in the case of the actual endoscope, structures can be observed from different directions and while moving. "Fly throughs", which are intended to give the impression of a virtual flight through the VOI, are possible. This is not only esthetic and instructive, but also may be of diagnostic value. In particular, a "vessel view" method can be used to render the interior of an evaluation volume visible.

For a parallel projection, a "maximum intensity projection" (MIP) or generally the "volume rendering" (VR) is particularly suitable. In the case of an MIP, the pixel with the highest CT value is determined in the projection direction along the search beam. In that case, the pixel value thus corresponds to the maximum CT value on the search beam.

In the case of the VR, not just a single pixel is chosen for each individual search beam coming from the observer's eye, but rather all CT values along the search beam can, with suitable weighting, deliver a pixel as a contribution to the resulting image. Freely selectable and interactively alterable transfer functions are used to assign opacity and color to each pixel value. It is thus possible, by way of example, to select normal soft tissue to be largely transparent, contrasted vessels to be slightly opaque and bones to be very opaque.

A prerequisite for image display in virtual endoscopy is normally a statement relating to an observer path. Such an observer path is also called a flight path or a center line. The observer path corresponds in practice to the path which is taken by a virtual endoscope head and along which a perspective view of the close surroundings is reproduced. In this case, the problem frequently arises that a body part to be examined in the VOI is split into a plurality of evaluation volumes.

In that case, there is no continuous observer path through the VOI. Rather, it is necessary to provide an observer path in the first evaluation volume and then to change to a second evaluation volume, with an observer path then needing to be provided again there. Such a situation may arise, by way of example, when a tubular formation in the VOI, for example a colon, a cisterna or a bronchial system, has a restriction or a closure or is interrupted in another way, for example is not filled with contrast agent, or other circumstances lead to the tubular body part on which the endoscope is to be used not being in the form of a single complete evaluation volume.

In this regard, a user of the usual method who is examining a patient normally needs to find the respective first and second evaluation volume and to define the conditions, e.g. a starting point, for an observer path from the very beginning. In that case, the examiner needs to use a large part of his time to find all evaluation volumes in order to examine the entire VOI. A new observer path needs to be provided in every single evaluation volume. This costs time and results in the "fly through" needing to be interrupted or even parts of the VOI not being examined.

It would be desirable for a virtual endoscopy to involve a VOI being examined as reliably and completely as possible.

SUMMARY

An object of an embodiment of the invention includes specifying a method of virtual endoscopy and/or a corresponding apparatus which can be used to perform a virtual endoscopy particularly simply and reliably. In particular, an observer path should be determined in a particularly expedient fashion, even if a number of evaluation volumes make up the VOI.

An object may be achieved for the method by a method of virtual endoscopy for medical 3D image display and processing which includes:
   automatic ascertainment of at least one further evaluation volume, which is separate from the first evaluation volume, on the basis of the 3D data volume according to predetermined criteria.

In this context, an embodiment of the invention includes the consideration that when a first evaluation volume in the VOI is provided, the characteristic features of the evaluation volume are already defined, and/or at any rate are sufficiently well known. These may be geometric or medical features, for example.

Such features can be used, on the basis of the recognition of an embodiment of the invention, as predetermined criteria for automatically ascertaining at least one further evaluation volume on the basis of the 3D data volume. The examiner thus does not himself need to search for all evaluation volumes in order to prepare a complete image of the VOI.

In a particular example embodiment, the concept proposed here has the advantage that this basis allows largely automatic calculation of the observer path through the complete VOI, even if the latter is in the form of a number of separate evaluation volumes. The same applies to a single evaluation volume which, although it is present in its entirety, has a geometry which is curved or bent or provided with other drastic changes of direction such that it is normally not possible to indicate a continual observer path through the VOI immediately.

A first and a further evaluation volume are thus also understood to include a first region and a further region of a cohesive VOI in which the first region and the further region are separated from one another, e.g. by a drastic restriction or constriction, to the extent that an examiner in practice has a first evaluation volume and a further evaluation volume available for a screen examination.

An evaluation volume is normally in the form of a tubular formation, as can often be found for a colon, a cisterna or a bronchial system.

Preferably, a further observer path may be provided through the at least one further evaluation volume. This allows, in practice, complete automatic calculation of an observer path through a number of evaluation volumes which are each there separately, that is to say even for the case in which a continuous observer path cannot be found between all evaluation volumes or can be found only under difficult circumstances. One development thus has provision, in particular, for automatic ascertainment for the case in which along the observer path the observer path allows a boundary to be identified for the evaluation volume.

Calculation of the observer path in line with the proposed concept may preferably be effected, in a first variant, through automatic ascertainment before the actual 3D image display and processing along the observer path. Alternatively or in addition, in a second variant, automatic ascertainment of the observer path may also be effected during the actual 3D image display and processing along the observer path.

In the case of the first variant, the observer path is determined by the "center line" within the context of an advance calculation. In the case of the second variant, the observer path is calculated as a "center line" during the "fly through", for example under the assumption that the "maximum visibility" corresponds to the desired direction of flight. In that case, online calculation of the observer path is thus involved.

In both cases, there is provision for automatic ascertainment of at least one further evaluation volume for the case in which during or upon the actual 3D image display and processing along the observer path of the first evaluation volume the observer path allows a boundary to be identified for the first evaluation volume.

Preferably, the at least one further evaluation volume is automatically ascertained starting from an orientation point or boundary for the observer path in the first evaluation volume. In this case, an orientation point is to be understood, in particular, to include a point from which a boundary for the first evaluation volume can be identified. In line with this development, there is thus automatic ascertainment from a position in the first evaluation volume at which the observer path in the first evaluation volume ends in practice.

It has been found that an observer path is defined particularly well only if the VOI, that is to say normally a tubular structure, is filled completely with contrast agent, for example in the form of an inert gas such as ambient air or $CO_2$, or with water. An unforeseen restriction or break in the VOI into individual evaluation volumes is frequently the case with a body which is to be examined and which is normally moving (breathing movement, muscular movement, blood circulation, operations), so that it is no longer readily possible to calculate an observer path.

Accordingly, within the context of one particularly preferred development, the entire VOI with all, particularly contrast-agent-filled, components is first of all visited, particularly automatically. The entire VOI is then preferably segmented into its components. Suitable selection of a component allows a first evaluation volume to be determined particularly expediently. Automatic ascertainment of at least one further evaluation volume is preferably supported by interactive selection or deselection of evaluation volumes which have not been recorded or which have been recorded incorrectly.

Further developments of embodiments of the invention make provision for further aids to assist the examiner within the context of the concept.

Preferably, there is provision for production of an assessment of the at least one further evaluation volume and of an assessment of options in this regard according to the predetermined criteria. The further evaluation volume found according to geometric and/or medical criteria naturally corresponds to such criteria to a greater or lesser extent. Such correspondence can be quantified within the context of an assessment. It is thus possible to indicate, by way of example, how high the likelihood is that the further evaluation volume, like the first evaluation volume, belongs to the same VOI, i.e. to the same body part that is to be examined, e.g. a large intestine.

Preferably, the examiner is provided with a number of further evaluation volumes and options in this regard for selection. This has the advantage that the examiner is able, for example as part of a menu selection, to make a reliable decision about the type of further selection options.

Preferably, the number of further evaluation volumes and options in this regard is sorted using the predetermined criteria. By way of example, the number of further evaluation volumes can be sorted using decreasing likelihood.

Examples of preferable predetermined criteria are geometric criteria, particularly relating to the size, the orientation and the shape of the evaluation volume. If a further evaluation volume has more or less the same properties as a first evaluation volume in terms of these criteria, then the likelihood is very high that it is the same VOI, that is to say the same body part which is to be examined.

In addition, it is possible to indicate medical criteria for producing the assessment, particularly relating to the type and surface condition of the evaluation volume. By way of example, the surface condition of an intestinal wall has a characteristic form in comparison with that of other parts of the body.

Preferably, the observer path is provided on the basis of an observer position and a path direction. Starting from an observer position, the virtual endoscopy can be effected along a path direction until a rectilinear observer path arising in this manner leads to the boundary of an evaluation volume. Should a boundary be in "sight", then either automatic ascertainment of at least one further evaluation volume or a change of direction can take place.

At least one embodiment of the method has been found to be particularly expedient for use in medical image display and processing of images, particularly of computed tomography or magnetic resonance images, of a colon, that is to say in colonoscopy. The concept has likewise been found to be advantageous for medical image display and processing of images, particularly of computed tomography or magnetic resonance images of a bronchial tree, that is to say in bronchoscopy. At least one embodiment of the method may likewise be advantageous for image display and processing of images, particularly of computed tomography or magnetic resonance images, of a cisterna, that is to say in cisternoscopy.

With regard to the apparatus, an embodiment of the invention provides a computer tomograph or a magnetic resonance tomograph which has control elements for at least one embodiment of the method in line with the concept explained above.

In addition, an embodiment of the invention provides a workstation for image display and processing of computed tomography or magnetic resonance images which has control elements for at least one embodiment of the method in accordance with the concept explained above.

Further, in an embodiment, a computer program product for image display and processing of computed tomography or magnetic resonance images has program modules for at least one embodiment of the method in accordance with the concept explained above.

BRIEF DESCRIPTION OF THE DRAWINGS

Example embodiments of the invention are described below with reference to the drawings. Specifically, in the drawings.

DETAILED DESCRIPTION OF THE EXAMPLE EMBODIMENTS

Figure 1:
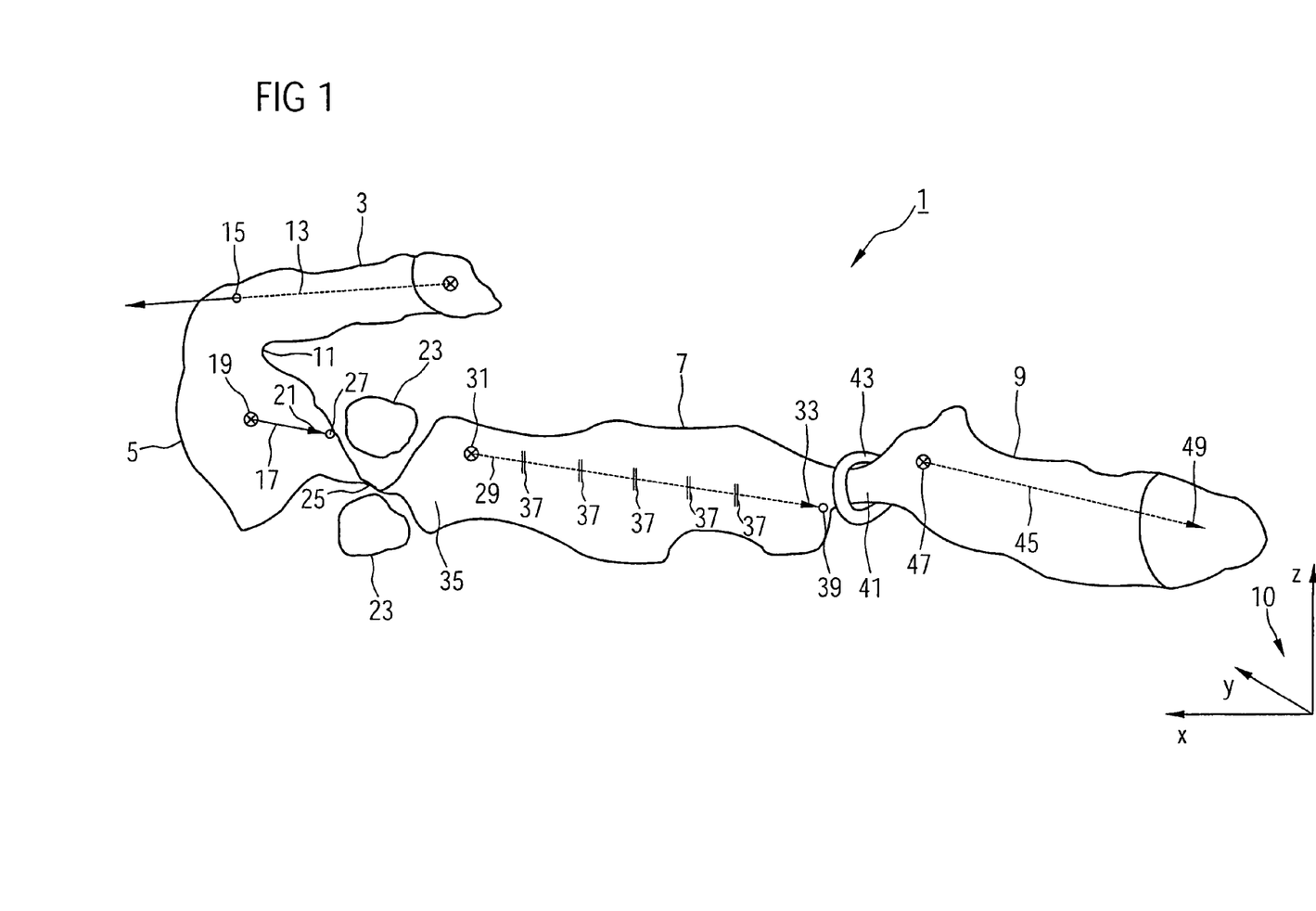
FIG. 1 shows an ordinary procedure, shown by way of example, for determining an observer path through a VOI with a number of evaluation volumes.

FIG. 1 shows an ordinary procedure for prescribing an observer path as part of a method of virtual endoscopy. In the present case, the explanation is given using the example of image display and processing of computed tomography images of a colon, that is to say using the example of a virtual endoluminal colonoscopy.

FIG. 1 shows a volume of interest (VOI) 1 with a first evaluation volume 3 and further evaluation volumes 5, 7, 9. The evaluation volumes 3, 5, 7, 9 are parts of a colon on the basis of a 3D data volume indicated in the form of a coordinate cross. Although the VOI 1 is a tubular body part which needs to be examined in total, namely in the present case the large intestine as one part of the colon, the VOI 1 is presented to the examiner during the screen examination in a winding form such that it is not possible to find a continuous observer path.

The first evaluation volume 3 is separated from the second evaluation volume 5 by a bend 11, for example. The curvature in the region of the bend 11 is so great that it is not possible to find a continuous path between the first evaluation volume 3 and the second evaluation volume 5. An observer path 13 defined in the course of an advance calculation hits the end point 15 at the boundary of the first evaluation volume 3. The examiner is therefore forced to indicate a new observer path 17 in the form of a new observer position 19 and of a new path direction 21 in the second evaluation volume 5. To do this, he first needs to find the second evaluation volume 5. In practice, the end point 15 marks the end of the observer path 13 in the first evaluation volume 3.

The second evaluation volume 5 has been pressed together in the region of a lesion 23 to form a closure 25. Thus, the further observer path 17 also hits the boundary of the second evaluation volume 5 at the end point 27. Again, the examiner needs to find a third evaluation volume 7 and to indicate a new observer path 29 in the form of an observer position 31 and a path direction 33.

Disadvantageously, a region 35 of the third evaluation volume 7 remains unexamined in this case, during the flight for the virtual endoscopy the new observer path 29 is respectively continued at the points 37 by a maximum visibility in the same direction of flight 33. In the present case, the endoluminal view of the third evaluation volume 7 is thus produced in the course of an online calculation of the observer path 29.

The observer path 29 again hits the boundary of the third evaluation volume 7 at an end point 39. In the present case, this is caused by a restriction 41 in the VOI 1 as a result of a muscle 43. A restriction might also be caused by too little contrast agent. For this reason, it is again necessary to indicate a new observer path 45 in the fourth evaluation volume 9 in the form of an observer position 47 and a path direction 49.

The outlined procedure is found to be difficult, time-consuming and at the same time unreliable in the case of the virtual endoscopy, since it is possible for regions 35 to escape examination, for example. This applies equally to a colonoscopy which is shown here, but also similarly to the virtual endoscopy in the region of the bronchoscopy and cisternoscopy or in other regions.

Figure 2:
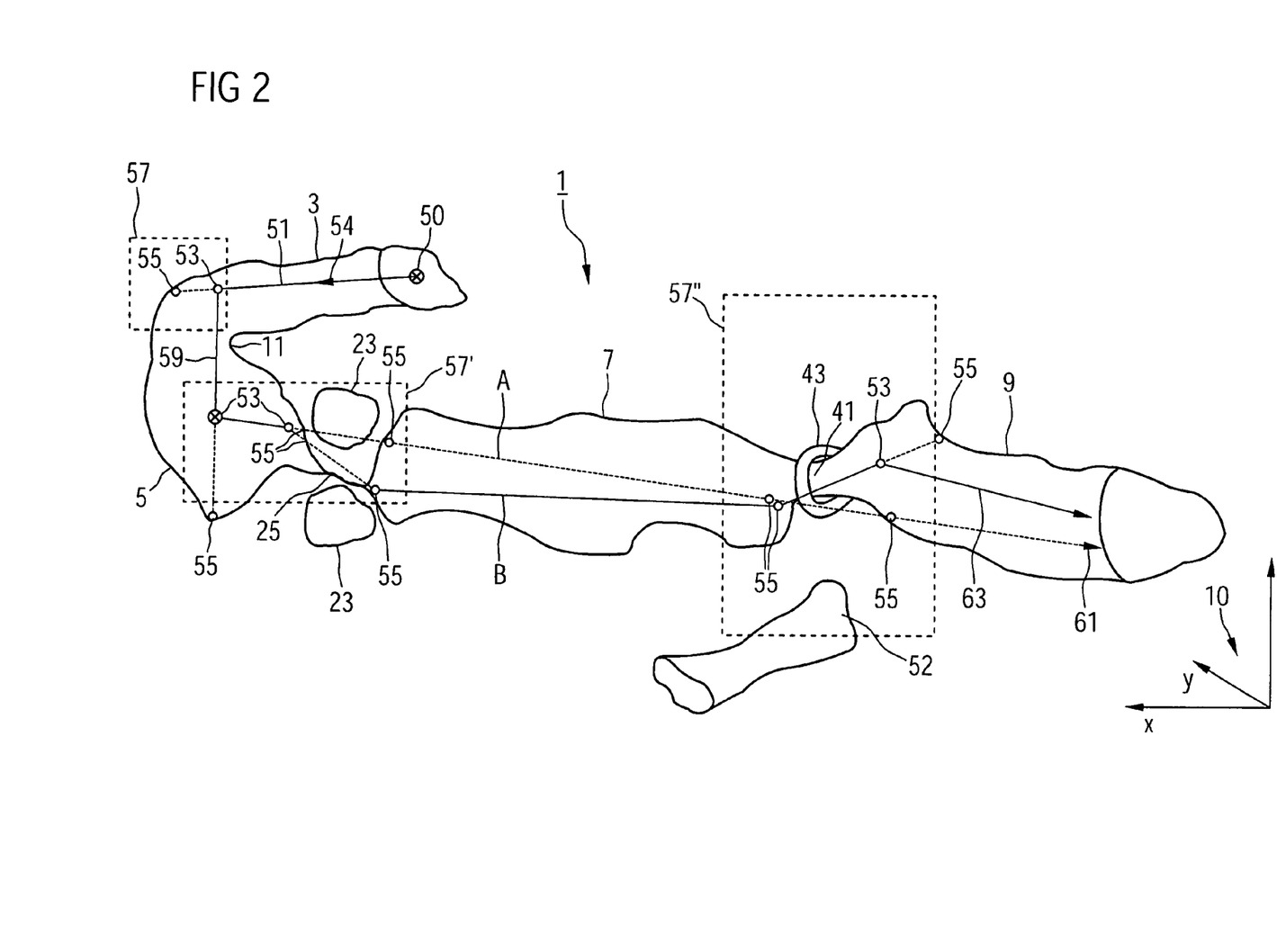
FIG. 2 shows an example embodiment of a procedure for determining an observer path through a VOI with a number of evaluation volumes.

One example embodiment of the concept proposed here for a method of virtual endoscopy is outlined using the same example of a large intestine as part of a colon and as VOI in FIG. 2. In this case, the same parts of the figure have been provided with the same reference symbols.

In line with the example embodiment, a first evaluation volume 3 of the large intestine is provided on the basis of a 3D data volume 10, and an observer path 51 is prescribed through the first evaluation volume 3. The observer path may be prescribed automatically and achieved with the aid of a computer.

If appropriate, the automatic prescribing is based on a statement by the examiner, e.g. relating to a starting point 50 and a direction 54 for the observer path 51. In this respect, the examiner is provided with an observer path 51. At an orientation point 53, the observer path 51 allows a boundary 55 for the evaluation volume 3 to be identified. Normally, such an orientation point would be the end of an observer path 51 in practice. A similar situation arises for the second evaluation volume 5, for the third evaluation volume 7 and for the fourth evaluation volume 9, which is why the corresponding orientation points 53 and boundaries 55 are identified using the same reference symbols.

In the regions 57, 57' and 57" (identified symbolically by frames) of the VOI 1, at least one further evaluation volume is therefore automatically ascertained on the basis of the 3D data volume 10 according to predetermined criteria. In the region 57 of the first evaluation volume 3, the second evaluation volume 5 is ascertained automatically. In this case, the predetermined criteria are primarily medical criteria, since the second evaluation volume 5 is found to be equivalent to the first evaluation volume 3 in terms of the type and surface condition.

The examiner can interactively prescribe a further observer path 59 or can have a further observer path prescribed automatically through the second evaluation volume 5. In this case, by way of example, the examiner can make a graphical selection of the evaluation volume 5 from a list of options.

In the region 57' of the second evaluation volume 5, a third evaluation volume 7 is ascertained automatically, although the closure 25 indicates that it is not possible to find a continuous path. Geometric criteria relating to size, orientation and shape of the evaluation volume 7 indicate that the latter is identified as being associated with the same VOI 1 as the second evaluation volume 5.

In this case, the examiner can select a new observer path A, for example, which in practice keeps the same orientation 61 in the second evaluation volume 5, in the third evaluation volume 7 and in the fourth evaluation volume 9. In addition, it is also possible for the examiner to have a computer indicate to him a new observer path B in the third evaluation volume 7 which is better suited to the closure 25.

In this context, both the observer path A and the observer path B can be provided as part of an advance calculation (described above) or as part of an online calculation (described above).

The situation explained is repeated in similar fashion in the region 57" between the third evaluation volume 7 and the fourth evaluation volume 9. In the region 57", the fourth evaluation volume 9 is automatically ascertained on the basis of predetermined geometric and/or medical criteria. The examiner is able to prescribe a further new observer path 63 for the fourth evaluation volume 9 or to have one indicated to him.

Should the examiner incorrectly be provided with the muscle 43 as a selectable option for an evaluation volume, for example, then the muscle 43 would nevertheless automatically be assessed with a much lower likelihood in the course of the method on account of its geometric and medical properties which differ greatly from those of the third evaluation volume 7 and those of the fourth evaluation volume 9. It would also be possible to provide an examiner with part 52 of a small intestine as an option for a further evaluation volume.

In line with an embodiment of the proposed method, the part 52 of the small intestine is assessed with a low likelihood on account of its geometric situation (since it is not on the same axis as the evaluation volume 7, 9) and the fact that no end of the part 52 indicates a closure. In addition, the part 52 as part of the small intestine does not have a start and has a different diameter than the evaluation volumes 7, 9, which are part of the large intestine of interest (VOI).

In this case, an examiner would thus be provided with the fourth evaluation volume 9 for selection with highest priority and would be provided with the muscle 43 and the part 52 of the small intestine for selection with a negligibly small degree of likelihood, if at all. Suitable sorting carried out on the basis of the assessment indicates the examiner is thus able to select the fourth evaluation volume 9 correctly as part of the VOI 1 reliably and quickly.

Figure 3:
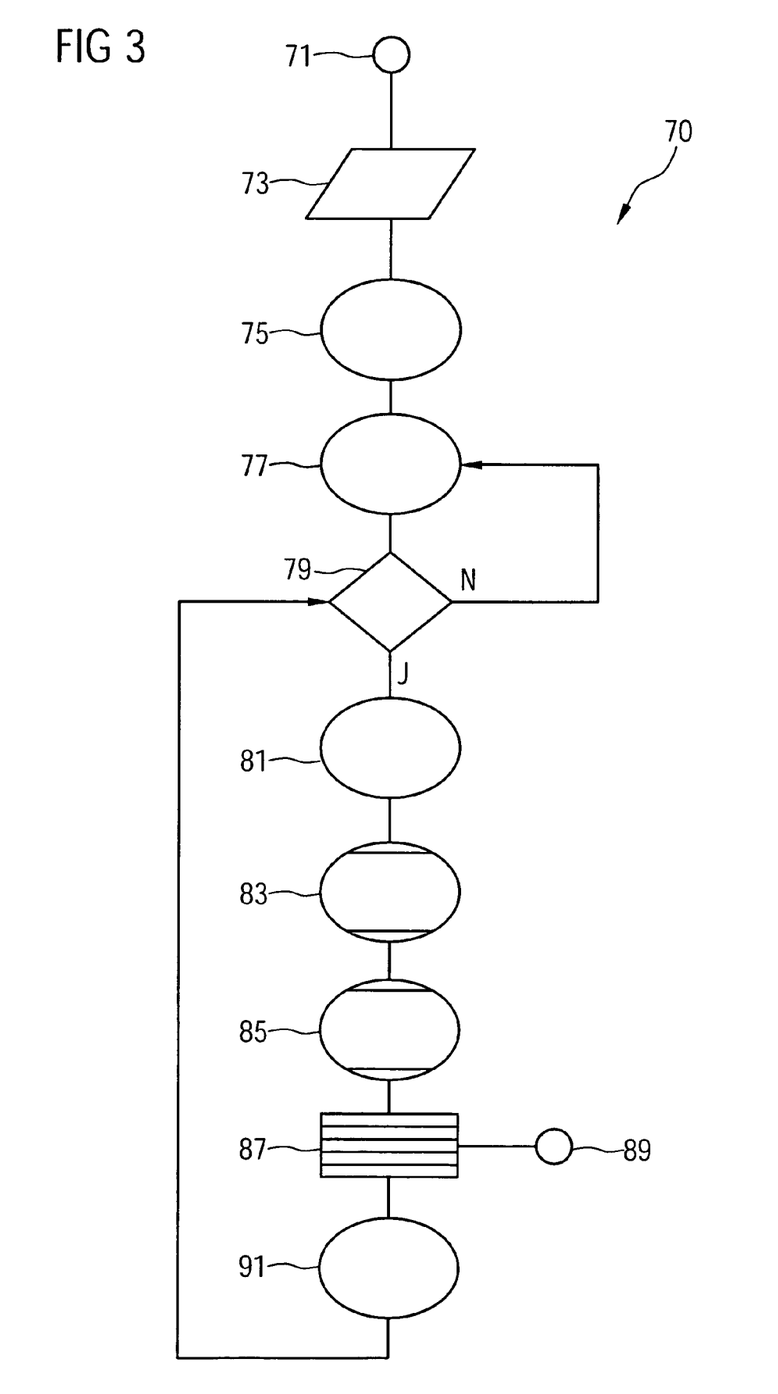
FIG. 3 shows a diagrammatic flowchart of an example embodiment of the method.

FIG. 3 schematically shows a flowchart of an embodiment of the method of virtual endoscopy. After the start of the method 71, a 3D data volume is provided in method step 73 and the 3D data volume is taken as a basis for providing a first evaluation volume in method step 75. The virtual endoscope is positioned automatically in the evaluation volume. This can be done using a 3D data volume 10 as shown in FIG. 2 and a first evaluation volume 3, for example. The software, possibly on the basis of the statements by an examiner, e.g. relating to observer position and path direction, then prescribes an observer path through the first evaluation volume in method step 77. This may be a first observer path 51 shown in FIG. 2, for example.

In the case of the embodiment shown in FIG. 3, method step 79 checks whether or not a boundary can be identified for the evaluation volume. This may be a boundary 55 shown in FIG. 2, for example, which is identified at an orientation point 53.

If a boundary is not identified, then the original observer path is followed further as part of the "fly through" in the branch N. If a boundary is identified, the branch Y is followed.

This results in at least one further evaluation volume being ascertained automatically on the basis of the 3D data volume according to predetermined criteria. This step is carried out, by way of example, in the regions 57, 57' and 57" shown in FIG. 2 by automatically ascertaining the further evaluation volumes 5, 7, 9. In method cycle 70, this process is shown by method step 81.

If a number amounting to a plurality of evaluation volumes is ascertained, these are assessed in a method step 83 and are sorted in a method step 85 using a falling assessment. In the case of an embodiment of a method cycle 70 which is shown in FIG. 3, sorting takes place such that the evaluation volumes assessed as having high likelihood are shown before the evaluation volumes assessed as having low likelihood. An examiner is thus actually provided with a sequentially falling, presorted selection of evaluation volumes in a method step 87, with the evaluation volume having the highest likelihood being shown in first place.

The selection can be made either in list form or as a graphical representation of the optional evaluation volumes (e.g. 7, 9, 52, 43) or of orientation points 53 or boundary 55, for example. The examiner can abort the method in method step 89 if he considers this to be expedient. Otherwise, he can continue the method with method step 91 through interactive or automatic selection of a further observer path in the further evaluation volume. By way of example, the further observer path used may be an observer path 59, A, B, 63 in FIG. 2.

The method continues in a loop in which a check for a boundary for the evaluation volume is carried out again for a new observer path.

An embodiment of the invention specifies a method of virtual endoscopy for 3D image display and processing in computed tomography which has the following method steps:

a first evaluation volume 51 is provided on the basis of a 3D data volume 10, an observer path 51 is provided through the first evaluation volume 3.

To allow automatic calculation of the observer path—even when it is not possible to find a continuous path through the VOI—the present concept provides for automatic ascertainment at least of a further evaluation volume 5, 7, 9 on the basis of the 3D data volume 10 according to predetermined criteria.

Any of the aforementioned methods may be embodied in the form of a system or device, including, but not limited to, any of the structure for performing the methodology illustrated in the drawings.

Further, any of the aforementioned methods may be embodied in the form of a program. The program may be stored on a computer readable media and is adapted to perform any one of the aforementioned methods when run on a computer device (a device including a processor). Thus, the storage medium or computer readable medium, is adapted to store information and is adapted to interact with a data processing facility or computer device to perform the method of any of the above mentioned embodiments.

The storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, such as floppy disks (trademark), cassette tapes, and removable hard disks; media with a built-in rewriteable non-volatile memory, such as memory cards; and media with a built-in ROM, such as ROM cassettes.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method of virtual endoscopy for medical 3D image display and processing, the method comprising:

providing a first evaluation volume on the basis of a 3D data volume;

providing, by at least one processing device, an observer path through the first evaluation volume;

determining whether a boundary for the first evaluation volume is identifiable;

automatically ascertaining, if the boundary for the first evaluation volume is identifiable, at least one further evaluation volume on the basis of the 3D data volume according to predetermined criteria, the predetermined criteria being at least one of geometric and medical criteria of at least one further evaluation volume, and the at least one further evaluation volume being separate from the first evaluation volume;

sorting a number of further evaluation volumes and options using the predetermined criteria and according to the likelihood that the further evaluation volume belongs to the same volume of interest (VOI) as the first evaluation volume; and provisioning a further observer path through the at least one further evaluation volume; wherein
- if the boundary for the first evaluation volume is not identifiable, an original observer path through the medical 3D image is followed,
- the geometric criteria relate to at least one of size, orientation, and shape of the further evalution volume, and
- the medical criteria relate to at least one of type and surface condition of the further evaluation volume.

2. The method as claimed in claim 1, further comprising:
automatically ascertaining the at least one further evaluation volume starting from an orientation point for the observer path in the first evaluation volume.

3. The method as claimed in 1, wherein the automatic ascertainment occurs before the actual 3D image display and processing along the observer path.

4. The method as claimed in claim 1, wherein the automatic ascertainment occurs during the actual 3D image display and processing along the observer path.

5. The method as claimed in claim 1, further comprising:
producing an assessment of the at least one further evaluation volume and an assessment of options in this regard according to the predetermined criteria.

6. The method as claimed in claim 1, further comprising:
provisioning the at least one further evaluation volume and options in this regard for selection.

7. The method as claimed in claim 1, wherein the observer path is provided on the basis of an observer position and a path direction.

8. The method as claimed in claim 1, wherein the method is for medical image display and the processing is an imaging method in at least one of computed tomography and magnetic resonance tomography.

9. The method as claimed in claim 1, wherein the method is for medical image display and processing of images of a colon.

10. The method as claimed in claim 1, wherein the method is for medical image display and processing of images of a bronchial tree.

11. The method as claimed in claim 1, wherein the method is for medical image display and processing of images of a cisterna.

12. At least one of a computer tomograph apparatus and a magnetic resonance tomograph apparatus, including at least one processing device for performing the method as claimed in claim 1.

13. A workstation for image display and processing of at least one of computed tomography and magnetic resonance images, including at least one processing device for performing the method as claimed in claim 1.

14. A computer program product for image display and processing of at least one of computed tomography and magnetic resonance images, the computer program product including a non-transitory computer readable medium, which further includes computer-executable instructions that when executed on a computer device cause the computer device to perform the method as claimed in claim 1.

15. The method as claimed in claim 1, further comprising:
automatically ascertaining the at least one further evaluation volume starting from at least one of a boundary and an orientation point for the observer path in the first evaluation volume.

16. An apparatus for virtual endoscopy for medical images in 3D, the apparatus comprising:
at least one processing device including,
- means for providing a first evaluation volume on the basis of a 3D data volume;
- means for providing an observer path through the first evaluation volume;
- means for automatically ascertaining, if the boundary for the first evaluation volume is identifiable, at least one further evaluation volume on the basis of the 3D data volume according to predetermined criteria, the predetermined criteria being at least one of geometric and medical criteria of at least one further evaluation volume, and the at least one further evaluation volume being separate from the first evaluation volume,
- means for sorting a number of further evaluation volumes and options using the predetermined criteria and according to the likelihood that the further evaluation volume belongs to the same volume of interest (VOI) as the first evaluation volume; and
- means for provisioning a further observer path through the at least one further evaluation volume; wherein
  - if the boundary for the first evaluation volume is not identifiable, an original observer path through the medical 3D image is followed,
  - The geometric criteria relate to at least one of size, orientation, and shape of the further evaluation volume, and
  - the medical criteria relate to at least one of type and surface condition of the further evaluation volume.

17. The apparatus as claimed in claim 16, wherein the apparatus is a workstation for image display and processing of at least one of computed tomography and magnetic resonance images.

* * * * *